United States Patent [19]

Sawyer

[11] Patent Number: 4,738,849
[45] Date of Patent: * Apr. 19, 1988

[54] COMPOSITE MEDICAL ARTICLES FOR APPLICATION TO WOUNDS AND METHOD FOR PRODUCING SAME

[75] Inventor: Philip N. Sawyer, Brooklyn, N.Y.

[73] Assignee: Interface Biomedical Laboratories Corp., Brooklyn, N.Y.

[*] Notice: The portion of the term of this patent subsequent to Aug. 19, 2003 has been disclaimed.

[21] Appl. No.: 945,115

[22] Filed: Dec. 22, 1986

Related U.S. Application Data

[60] Continuation-in-part of Ser. No. 877,078, Jun. 23, 1986, which is a division of Ser. No. 625,986, Jun. 29, 1984, Pat. No. 4,606,910.

[51] Int. Cl.$^4$ .................... A61L 15/00; A61L 17/00
[52] U.S. Cl. .................... 424/449; 514/801; 514/953; 128/156
[58] Field of Search .................. 424/449; 514/801; 128/156

[56] References Cited

U.S. PATENT DOCUMENTS

| | | | |
|---|---|---|---|
| 4,022,203 | 5/1977 | Ackley | 128/156 |
| 4,233,360 | 11/1980 | Luck et al. | 514/801 |
| 4,238,480 | 12/1980 | Sawyer | 424/177 |
| 4,390,519 | 6/1983 | Sawyer | 424/28 |
| 4,404,970 | 9/1983 | Sawyer | 128/325 |
| 4,407,787 | 10/1983 | Stemberger | 128/156 |
| 4,424,208 | 1/1984 | Wallace et al. | 514/801 |
| 4,453,939 | 6/1984 | Zimmerman et al. | 128/156 |
| 4,605,548 | 8/1986 | Ushiyama et al. | 424/449 |
| 4,606,337 | 8/1986 | Zimmermann et al. | 128/156 |
| 4,606,910 | 8/1986 | Sawyer | 128/156 |

Primary Examiner—Ronald W. Griffin
Attorney, Agent, or Firm—Pennie & Edmonds

[57] ABSTRACT

A composite medical article comprising a porous body, a first layer of a medicinal substance and a second layer of a medicinal substance. A method for forming a composite medical article comprising saturating a porous substrate so as to incorporate a first medicinal substance therein, preparing a coating therefor comprising a second medicinal substance with at least a portion thereof in liquid phase, affixing an onlay of the coating to the material by freezing the liquid portion of the coating to the material to form an onlaid composite medical article and drying the article. The medicinal substances may comprise either a hemostatic agent or a medicament.

35 Claims, 2 Drawing Sheets

COMPOSITE MEDICAL ARTICLES FOR APPLICATION TO WOUNDS AND METHOD FOR PRODUCING SAME

CROSS-REFERENCE TO RELATED APPLICATIONS

This application is a continuation-in-part of application Ser. No. 877,078, filed June 23, 1986, which is a divisional of application Ser. No. 625,986, filed June 29, 1984, now U.S. Pat. No. 4,606,910 on Aug. 19, 1986.

FIELD OF THE INVENTION

This invention relates to composite medical articles and to methods of preparing the same.

BACKGROUND

In various prior patents, I have shown how certain modifications of collagen, collagen-like compounds and gelatin could augment the hemostatic properties of such compounds by manipulation of the surface charge and microstructure thereof. In U.S. Pat. No. 4,238,480, I disclosed that an improved hemostatic agent could be made by treating collagen or collagen-like substances to render the surface charge effectively more positive and that the thusly modified substance could be employed to control or terminate bleeding.

Other references relate to the provision of liquid absorbent patches, pads or the like to carry medicaments. For example, in U.S. Pat. No. 4,022,203, Ackley discloses a liquid absorbable pad means containing a quantity of blood coagulating substance to reduce blood flow. In U.S. Pat. Nos. 4,390,519 and 4,404,970 I disclosed that a modified blood-soluble hemostatic agent could be combined with or incorporated into a porous or supporting body such as, for example, a gauze pad, a bandage, a laparotomy pad or a sponge. By embodying the improved hemostatic agent into such porous body, the resulting article itself becomes a hemostatic material possessing the properties of the agent and may be applied to an area of trauma or injury where such properties may be utilized.

I have now discovered that there are certain additional advantages which result from the use of a composite medical article if an onlay of a medicinal substance can be fused to the surface of an article which has already been impregnated with the same or a different medicinal substance so that the medicinal onlay is the first to come in contact with an area of trauma or injury.

SUMMARY OF THE INVENTION

The provision of a coating of a medicinal substance to a porous body which is already impregnated with the same or a different medicinal substance will have a number of advantages in clinical application over the composite medical articles known previously. The different porous materials in which medicinal substances may be incorporated —gauze, sponge, tissue, etc.—have different absorbencies and different effects on the healing rate of a wound to which the materials may be applied. The provision of a coating of a medicinal substance, which absorbs serum and plasma from an injured area, will make the effects produced by use of the differing materials more uniform by mitigating any problems which may be encountered in dealing with a particular substrate in clinical use. In addition, if the coated medicinal substance is more absorbent of serum and plasma from an injured area than is the material which it coats, the provision of such coating has been found to relieve pain in a patient more rapidly than will the material without such coating. For example, a hemostatic agent as disclosed in my U.S. Pat. No. 4,238,480 will have this effect. Further, the provision of a second layer of a medicinal substance, into which has been absorbed a first layer of the same or a different medicinal substance, as a coating on the surface of a porous bandage or dressing, can have a comforting effect on a patient by acting as a cushion between the wound and the coated material.

By medicinal substance, what I mean is any agent having a therapeutic effect on cuts, burns, wounds, trauma, injuries and the like. These substances include both hemostatic agents, which are prepared by modifying a collagen or a collagen-like substance by dissolving it in water and then rendering the surface charge effectively more positive than prior to the modification while retaining the water solubility of the substance; and medicaments which are defined as an agent or substance which assists in the recovery from illness or trauma, which includes compositions having antibacterial, fungicidal or antibiotic effects, burn ointments and salves, lubricating agents such as petroleum jelly, proteins such as albumen and polymers which permit breathing of injured tissue to facilitate healing thereof.

It is an object of the invention to provide an improved composite medical article comprising a porous substrate, a first layer of a medicinal substance and a second layer of the same or a different medicinal substance upon at least a portion of the first layer and preferably bonded thereto.

It is another object of the invention to provide an improved method for preparing such composite medical articles.

To achieve the above and other objects of the invention, there is provided a method which comprises incorporating a first medicinal substance into a porous body, preparing a coating of a second medicinal substance with at least a portion thereof in liquid phase, affixing an onlay of said second medicinal substance to the coated material by freezing the liquid portion to said material to form an onlaid composite medical article, and drying the article.

According to a feature of the invention the composite medical article may be coated upon one surface with a first layer of a medicinal substance such as a hemostatic agent or a medicament to which has been bonded a second layer of a medicinal substance which may be composed of the same or a different hemostatic agent or medicament or a mixture thereof. Conversely, the article may be coated upon its opposed surfaces with either the same or different medicinal substances.

According to a further feature of the invention, the coated material is prepared by freezing the first medicinal substance in the porous body. The porous body may preferably be saturated with said first medicinal substance prior to said freezing step.

According to a preferred embodiment of the invention, the medicinal substance to be applied as a second layer upon the composite article may be prepared with at least a portion thereof in the liquid phase by first freezing either or both of these agents and then melting at least the surface of the thusly frozen second agent.

According to the invention, there is provided a composite medical article and an apparatus for producing such improved composite medical articles prepared as indicated above. The apparatus comprises a coating means for applying a liquid layer of a medicinal substance to a porous body which has been saturated or substantially saturated with either an identical or a different medicinal substance, freezing means for fusing a first liquid layer of the medicinal substance to a second layer of the same or a different such agent, drying means for drying the fused layers of said first and said second layers of said medicinal substances, and conveyor means cooperating with said coating, freezing and drying means for furnishing a strip of said porous material to said coating, freezing, and drying means respectively.

BRIEF DESCRIPTION OF DRAWINGS

FIGS. 1-6 are schematic representations of a sequence of operations illustrating a method of the invention.

DETAILED DESCRIPTION

This disclosure incorporates herein by reference the drawings and disclosures of my prior U.S. Pat. Nos. 4,238,480; 4,390,519 and 4,404,970.

Figure 1:

With reference to FIG. 1, a medicinal substance 2 is placed in a vessel 4 in the liquid phase. In accordance with one embodiment of the invention, the medicinal substance may comprise a hemostatic agent, i.e., a collagen substance or a collagen-like substance which has been modified by dissolving the substance in water and modifying the thusly dissolved substance to render the surface charge thereof effectively more positive than prior to modification, in manners which are shown, for example, in my earlier U.S. Pat. No. 4,238,430. Such modified collagen or collagen-like substances may be prepared as taught in said U.S. Pat. No. 4,238,480 and may be freeze dried. The thusly modified and freeze dried hemostatic agent may be dissolved in water for use as the hemostatic agent(s) of the present invention. Alternately, the medicinal substance may also comprise one of the medicaments referred to above.

Figure 2:

As shown diagrammatically in FIG. 2, medicinal substance 2 in the vessel 4 may then be frozen into the solid phase. Reference numeral 2' is used to designate the medicinal substance in the solid, as opposed to liquid, phase.

Figure 3:
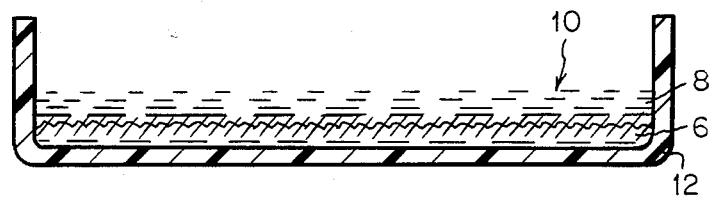

As shown in FIG. 3, a porous body 6 incorporating one or a combination of said medicinal substances 8 therein forms a coated medical article 10 which is placed in a container 12. The medicinal substance 8 may be of the same or of substantially the said chemical composition as the medicinal substance 2 shown in FIG. 1. In other words, both medicinal substances may comprise the same or substantially the same hemostatic agent, prepared as described above or one may choose to apply multiple layers of the same or substantially similar medicaments to porous body 6. These medicinal substances may be incorporated into a porous body such as, for example, a bandage, a small gauze sponge, a pad of surgical gauze, a laparotomy pad, a small sponge of natural or synthetic material or the like as shown, for example, in my earlier U.S. Pat. No. 4,404,970. As shown in the said patent, a medicinal substance such as a hemostatic agent 8 may be incorporated in the porous body by, for example, freezing and drying or vacuum drying the agent in the porous body.

The following lyophilization techniques may be used relative to the disclosure set forth above as to the use of hemostatic agents:

1. Dispense 50 ml amounts into plastic 100 mm petri dishes.
2. Shelf-freeze in lyophilizer (e.g., Vitrus model 100 SRC-7) at minus 30° to minus 50° C. for 3 to 5 hours, or until eutectic point has been determined.
3. Set condenser for one to two hours; begin vacuum with no heat for three hours.
4. Set shelf heat to plus 30° C. and continue for 48 hours.

Gamma irradiation may be used for sterilization. The following may alternatively be used for sterilization:

1. Place in sterilization envelope and seal with indicator inside.
2. Gas sterilize with ethylene oxide through normal cycle. (Alternatively gamma ray sterilization with Cobalt irradiation to greater than 20 megarads.)
3. Aerate thoroughly following exposure to ethylene oxide.

According to a preferred embodiment of the invention, the porous body 6 will be saturated with a medicinal substance 8 in the liquid phase. The mixture of liquid medicinal substance 8 as absorbed in porous body 6 may then be frozen as illustrated diagrammatically in FIG. 4.

Referring now to FIG. 5, the porous substrate 10 with the frozen medicinal substance 8 incorporated thereinto is placed on top of a second frozen layer of the same or a different medicinal substance 2' in vessel 4. The surface of this second layer 2' is melted (melted portion designated by reference numeral 2) by methods well known in the art. The additional medicinal substance 2' is then fused to the saturated porous substrate 10 by refreezing the melted portion 2 of medicinal substance 2' to material 10. The resultant composite medical article may then be freeze dried or vacuum dried to remove water therefrom. FIG. 6 shows a completed freeze-dried composite medical article wherein a second medicinal substance 2 has been fused to the face of a porous material saturated with a first medicinal substance 10 and subsequently freeze dried or vacuum dried.

Figure 7:
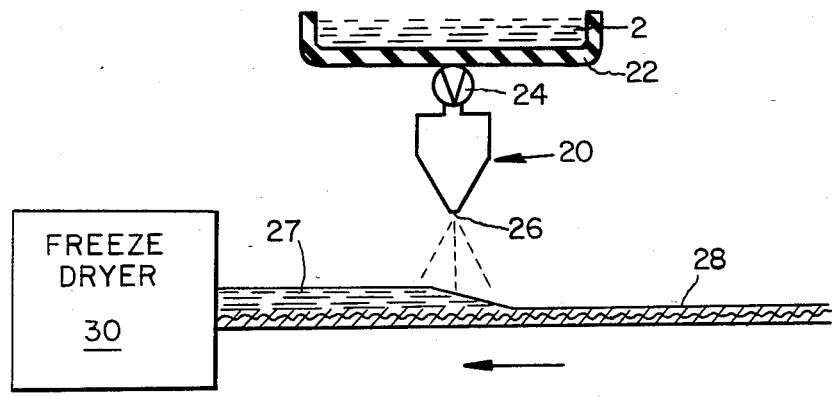
FIG. 7 is a diagramatic view of an apparatus of the invention.

An apparatus for the application of an onlay of a medicinal substance to a continuous strip of a porous substrate which is saturated with the same or a different medicinal substance in accordance with the principles of the invention will now be described. As shown in FIG. 7, a second medicinal substance 2 can be applied as a liquid to a strip of a pre-coated porous substrate 28 by means, for example, of a spray applicator, indicated generally at reference numeral 20. Spray applicator 20 comprises a vat 22 containing medicinal substance 2 in liquid form. In one embodiment of the invention, the medicinal substance may comprise from 0.25 to 1.5% of an aqueous solution of a collagen or collagen-like substance which has been modified to render the surface charge of such substance effectively more positive than prior to modification in accordance with the teachings of U.S. Pat. No. 4,238,480.

In a further embodiment a medicament may be applied at a level which will provide a therapeutic effect. The thickness of the onlay should preferably range between 0.5 to 1 mm,. Nozzle 26 may be used to deposit one or more layers of medicinal substance 27 onto strip 28. Strip 28 comprises a already frozen, saturated mixture of a medicinal substance in, for example, a bandage. This may be prepared in accordance with the teachings of U.S. Pat. No. 4,390,519 or U.S. Pat. No. 4,404,970. A continuous layer of medicinal substance 2 may be deposited onto strip 28 by moving the strip relative to nozzle 26. Valve 24 may be used for regulating the flow of the material to be deposited through nozzle 26. A liquid layer of the medicinal substance 2 which is deposited on strip 28 may then be fused to said strip by passing said strip through a freezer dryer as indicated diagrammatically at 30.

Figure 8:
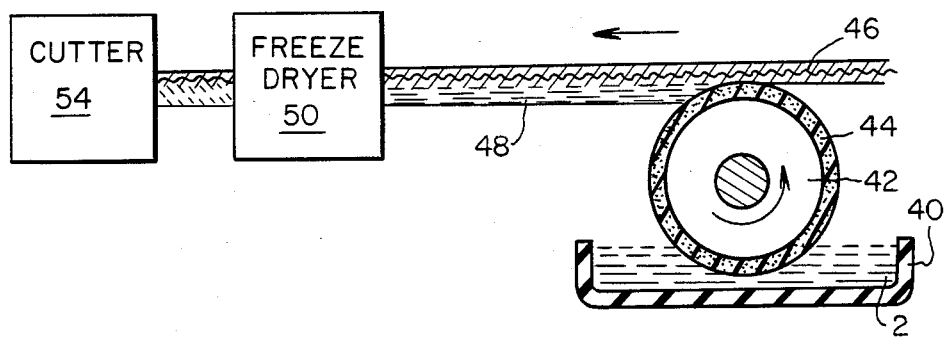
FIG. 8 is a diagramatic view of another apparatus of the invention.

An alternative apparatus for production of a continuous strip of a composite medical article in accordance with the invention is shown in FIG. 8. A strip of porous material 46 which has been saturated with a frozen medicinal substance is passed by a rotating cold wheel 42. The wheel is rotated through a vessel 40 containing either the same or a different medicinal substance or a mixture thereof. A medicinal substance such as a hemostatic agent, for example may be prepared, as discussed above, in accordance with the disclosure of U.S. Pat. No. 4,238,480. The solution may alternatively comprise up to 10% of hemostatic agent 2 or an effective amount of a medicament. The wheel comprises a liquid absorbent surface 44 which is a sponge or felt material or the like. The sponge or felt material 44 of the surface picks up the medicinal substance from vessel 40 and brings it into contact with the surface of strip 46 where it forms a second layer on the surface of the frozen material, as shown at 48. The coated porous substrate with an additional adsorbed layer of the same or a different medicinal substance is then advanced into a thin mouth, small volume, high energy, freeze dryer, as indicated diagrammatically at 50, to produce a composite medical article in a continuous strip. Cutting means, as indicated diagrammatically at 54, may also be supplied to cut the continuous strip into desired sizes.

There will now be obvious to those skilled in the art many modifications and variations of the above embodiments. These modifications and variations will not depart from the scope of the invention if defined by the following claims.

I claim:

1. A method for forming a composite medical article which comprises:
   incorporating a first medicinal substance into a porous body so as to saturate said body with said substance;
   preparing a second medicinal substance with at least a portion thereof in liquid phase;
   affixing an onlay of said second medicinal substance to said saturated body so as to form an onlaid composite medical article; and
   drying said article.

2. The method of claim 1 which further comprises freezing the liquid portion of said second medicinal substance to said saturated body so as to affix said onlay of said second medicinal substance.

3. The method of claim 1 wherein said first and said second medicinal substances are of substantially the same chemical composition.

4. The method of claim 1 wherein at least one of said medicinal substances is a medicament.

5. The method of claim 1 wherein at least one of said medicinal substances is a hemostatic agent.

6. The method of claim 5 which further comprises preparing said hemostatic agent by modifying one of the group consisting of a collagen or a collagen-like substance by dissolving the substance in water and modifying the thusly dissolved substance to render the surface charge thereof effectively more positive than prior to such modification while retaining the water solubility of the substance.

7. The method of claim 1 which further comprises preparing said porous body containing one of said medicinal substances for the addition thereto of a further medicinal substance, by freeze drying or vacuum drying said substance containing body.

8. The method of claim 7 wherein the porous body is saturated with the first medicinal substance.

9. The method of claim 1 wherein the second medicinal substance is incorporated into said porous body in liquid phase and is subsequently frozen thereonto.

10. The method of claim 1 wherein the second medicinal substance is prepared with at least a portion thereof in liquid phase by first freezing said second medicinal substance and then melting at least the surface of the thusly frozen second substance.

11. The method of claim 1 wherein said onlay of said second medicinal substance is affixed to said saturated body by rotating a wheel applicator through a vessel containing said second substance and past said saturated body respectively so that a quantity of said second substance is deposited initially on said wheel applicator and subsequently upon said saturated body with at least a portion of said second substance in liquid phase and freezing the liquid portion, of said second substance to said saturated body.

12. The method of claim 11 wherein the liquid portion of said second substance is frozen to said saturated body by passing said saturated body with said second substance deposited thereupon into a freezer.

13. The method of claim 1 wherein the onlay of said second medicinal substance is applied to said saturated body by spraying.

14. A method for forming a composite medical article which comprises:
   incorporating a first medicinal substance into a porous body so as to saturate said body; and
   applying a layer or coating of a second medicinal substance upon at least a portion of one surface of said saturated body.

15. The method of claim 14 wherein the step of affixing a layer or coating of a second medicinal substrate comprising applying to said saturated body said second medicinal substance, at least a portion of which is in the liquid phase, and drying said liquid phase portion to affix said layer or coating of said second medicinal substance upon said portion of one surface of said saturated body.

16. A method for forming a composite medical article which comprises:
   applying a first layer or coating of a first medicinal substance to at least one surface of a porous body; and
   applying a second layer or coating of a second medicinal substance to at least a portion of said first layer or coating.

17. The method of claim 16 wherein said first and said second medicinal substances are of substantially the same chemical composition.

18. A composite medical article prepared in accordance with claim 1.

19. A composite medical article prepared in accordance with claim 14.

20. A composite medical article prepared in accordance with claim 16.

21. A composite medical article comprising:
a porous body;
a first layer of a medicinal substance; and
a second layer of a medicinal substance upon at least a portion of said first layer.

22. The article of claim 21 wherein said first layer is absorbed within said porou body.

23. The article of claim 21 wherein said first layer is affixed to at least a portion of a surface of said porous 24. The article of claim 21 wherein said second layer is affixed to at least a portion of a surface of said porous 25. The article of claim 21 wherein said second layer covers substantially all of said first layer.

26. A composite medical article comprising:
a porous body;
a first medicinal substance incorporated into said porous body; and
a layer or coating of a second medicinal substance affixed to at least a portion of one surface of said porous body.

27. The composite medical article of claim 26 wherein said second medicinal agent substantially covers said porous body surface.

28. The composite medical article of claim 26 wherein at least one of said medicinal substances is a hemostatic agent comprising a modified collagen or collagen-like substance.

29. The composite medical article of claim 26 wherein at least one of said medicinal substances is a medicament.

30. The composite medical article of claim 26 wherein said porous body is selected from the group consisting of bandages, gauze, pads, strips and sponges, each comprised of a natural or synthetical material.

31. The method of claim 1 which further comprises preparing one or more additional medicinal substances having at least a portion thereof in liquid phase, and affixing an onlay of said one or more additional medicinal substances upon at least a portion of said second medicinal substance onlay prior to drying said article.

32. The method of claim 14 which further comprises applying a second layer or coating of a third medicinal substance upon at least a portion of said second medicinal substance layer or coating.

33. The method of claim 16 which further comprises applying a second layer or coating of a third medicinal substance upon at least a portion of said second medicinal substance layer or coating.

34. A composite medicinal article prepared in accordance with claim 33.

35. The composite medicinal article of claim 21 further comprising one or more additional layers of a medicinal substance upon at least a portion of said second layer.

* * * * *